(12) United States Patent
Hirano et al.

(10) Patent No.: US 9,393,224 B2
(45) Date of Patent: Jul. 19, 2016

(54) PROPHYLACTIC AND/OR THERAPEUTIC AGENT FOR CARDIOVASCULAR COMPLICATIONS OF DIABETES

(75) Inventors: Ken-ichi Hirano, Osaka (JP); Yoko Yasui, Osaka (JP); Yoshihiko Ikeda, Osaka (JP); Mitsutoshi Setou, Shizuoka (JP); Nobuhiro Zaima, Shizuoka (JP)

(73) Assignees: OSAKA UNIVERSITY, Osaka (JP); NATIONAL CEREBRAL AND CARDIOVASCULAR CENTER, Osaka (JP); NATIONAL UNIVERSITY CORPORATION HAMAMATSU UNIVERSITY SCHOOL OF MEDICINE, Shizuoka (JP); KOWA COMPANY, LTD., Aichi (JP)

( * ) Notice: Subject to any disclaimer, the term of this patent is extended or adjusted under 35 U.S.C. 154(b) by 0 days.

(21) Appl. No.: 14/241,147

(22) PCT Filed: Aug. 27, 2012

(86) PCT No.: PCT/JP2012/071594
§ 371 (c)(1),
(2), (4) Date: Apr. 21, 2014

(87) PCT Pub. No.: WO2013/031729
PCT Pub. Date: Mar. 7, 2013

(65) Prior Publication Data
US 2014/0296338 A1   Oct. 2, 2014

(30) Foreign Application Priority Data
Aug. 26, 2011 (JP) .................................. 2011-184318

(51) Int. Cl.
| A61K 31/20 | (2006.01) |
| A61K 31/23 | (2006.01) |
| A61K 31/19 | (2006.01) |
| A61K 31/215 | (2006.01) |

(52) U.S. Cl.
CPC ................. *A61K 31/23* (2013.01); *A61K 31/19* (2013.01); *A61K 31/20* (2013.01); *A61K 31/215* (2013.01)

(58) Field of Classification Search
CPC .................................................... A61K 31/20
USPC ........................................................ 514/558
See application file for complete search history.

(56) References Cited

U.S. PATENT DOCUMENTS

| 4,916,239 | A | 4/1990 | Treiber |
| 5,753,703 | A | 5/1998 | Cavazza et al. |
| 2003/0114497 | A1 | 6/2003 | Alani et al. |
| 2003/0194440 | A1 | 10/2003 | Lofroth et al. |
| 2004/0132814 | A1 | 7/2004 | Loefroth et al. |
| 2004/0142018 | A1 | 7/2004 | Takeuchi et al. |
| 2005/0107446 | A1 | 5/2005 | Alani et al. |
| 2007/0031493 | A1 | 2/2007 | Lofroth et al. |
| 2010/0160435 | A1 | 6/2010 | Bruzzese |
| 2010/0286269 | A1 | 11/2010 | Pichette et al. |
| 2010/0291216 | A1 | 11/2010 | Lofroth et al. |
| 2010/0291217 | A1 | 11/2010 | Lofroth et al. |

FOREIGN PATENT DOCUMENTS

| CN | 101878028 A | 11/2010 |
| EP | 1 279 400 | 1/2003 |
| EP | 1279400 A1 * | 1/2003 |
| JP | 9-176005 | 7/1997 |
| JP | 2718422 | 11/1997 |
| JP | 2001-502671 | 2/2001 |
| JP | 2003-238399 | 8/2003 |
| JP | 2005-501051 | 1/2005 |
| JP | 2006-117557 | 5/2006 |
| JP | 2009-504588 | 2/2009 |
| WO | 03/007932 | 1/2003 |
| WO | 2008/105533 | 9/2008 |

OTHER PUBLICATIONS

Supplementary European Search Report dated Nov. 21, 2014 in EP Application No. 12826804.2.
English translation of the International Preliminary Report on Patentability.
R. Shibata et al., "Adiponectin and Cardiovascular Remodeling", Adiposcience, vol. 6, No. 2, pp. 127-132, Jun. 2009 (partial English translation).
K. Maeda et al., "Adipocytokine to Shinkekkan Shikkan", The Circulation Frontier, vol. 9, No. 3, pp. 18-25, Sep. 1, 2005 (partial English translation).
K. Ohashi et al., "Metabolic Syndrome to Jinshikkan, Adipocytokine, Adiponectin Zoki Shogai", Nephrology Frontier, vol. 5, No. 3, pp. 203-207, Sep. 30, 2006 (partial English translation).
H. Watada, "Metabolic Syndrome towa Donna Monoka?", Juntendo Medical Journal, vol. 54, No. 4, pp. 503-507, Dec. 26, 2008 (partial English translation).
N. Maeda et al., Journal of Japan Society for the Study of Obesity, vol. 10, No. 1, pp. 22-30, 2004 (partial English translation).
Su Ke et al, "Study of the effect of serum adiponectin level on insulin resistance and cardiovascular complications in patients with type 2 diabetes", Department of Internal Medicine, the Affiliated Hospital of Guilin Medical College, China, 2005, pp. 2135-2137, with English translation.
Changyong Xue et al., "A Kind of Bioactive Lipids: Medium Chain Fatty Acids and Their Effect on Lipid and Glucose Metabolism", Clinical Medication Journal, Jul. 2011, vol. 9, No. 4, pp. 1-7, with English translation.

* cited by examiner

*Primary Examiner* — Kevin E Weddington
(74) *Attorney, Agent, or Firm* — Wenderoth, Lind & Ponack, L.L.P.

(57) ABSTRACT

An object of the present invention is to provide a drug that contains a compound for inhibiting neutral lipid accumulation in cardiovascular tissue or cells and has an excellent prophylactic or therapeutic effect on cardiovascular complications of diabetes. The present invention relates to a prophylactic and/or therapeutic agent for cardiovascular complications of diabetes, the agent containing a compound (preferably a medium-chain fatty acid and/or a medium-chain triglyceride) for inhibiting neutral lipid accumulation.

11 Claims, 4 Drawing Sheets

PROPHYLACTIC AND/OR THERAPEUTIC AGENT FOR CARDIOVASCULAR COMPLICATIONS OF DIABETES

TECHNICAL FIELD

The present invention relates to a prophylactic and/or therapeutic agent for cardiovascular complications of diabetes. More specifically, the present invention relates to a prophylactic and/or therapeutic agent for cardiovascular complications of diabetes, the agent containing a compound capable of inhibiting accumulation of neutral lipid, degrading accumulated neutral lipid, and improving the metabolism of neutral lipid in cardiovascular tissue or cells, and improving vascular functions.

BACKGROUND ART

Conventionally, cholesterol receives attention as a lipid that causes congestive heart failure, arteriosclerosis, dementia, and the like, and arteriosclerosis, for example, has been believed to develop due to cholesterol accumulation in the vascular subendothelium. As a means for preventing or treating such diseases, various pharmaceutical formulations including statin drugs that target cholesterol have been developed (Patent Literature 1 to 3, for example).

It has become clear that reduction of cholesterol by such formulations decreased the incidence of cardiovascular disease by about 30%, for example, but the other 70% of the patients were not controlled, indicating that the effect is inadequate.

When used for diabetic patients, such cholesterol-lowering drugs showed effects on only about 20% of the patients in terms of treating diabetic cardiovascular complications including cardiovascular disease, indicating that such drugs are not effective enough.

Risk factors for arteriosclerosis are thought to include hypercholesterolemia, smoking, hypertension, diabetes, and obesity, and these risk factors are believed to promote the progress of arteriosclerosis. Therefore, managing or reducing such risk factors is generally thought to be effective in preventing or treating arteriosclerosis.

Aggressive management of such risk factors, however, has not yet successfully inhibited the development of cardiovascular complications in diabetic patients. Nor has surgical treatment (coronary angioplasty and bypass surgery, for example), which is one of the therapies for arteriosclerosis, been effective enough in treating diabetic arteriosclerosis. Therefore, development of a drug that is highly effective in treating diabetic cardiovascular complications in diabetic patients has been desired.

CITATION LIST

Patent Literature

Patent Literature 1: Japanese Patent No. 2718422
Patent Literature 2: Japanese Translation of PCT International Application No. 2001-502671
Patent Literature 3: Japanese Translation of PCT International Application No. 2005-501051

SUMMARY OF INVENTION

Technical Problem

An object of the present invention is to provide a drug that contains a compound for inhibiting neutral lipid accumulation in cardiovascular tissue or cells and has an excellent prophylactic and/or therapeutic effect on diabetic cardiovascular complications.

Solution to Problem

The inventors of the present invention conducted intensive research to solve the above problem and, as a result, found that there exists a condition of arteriosclerosis where no cholesterol accumulates in blood vessels but instead neutral lipid accumulates in cardiac blood vessels. They also found that application of a medium-chain fatty acid and/or a medium-chain triglyceride in diabetic cardiovascular complications exhibits an excellent prophylactic and/or alleviating effect on diabetic cardiovascular complications with neutral lipid accumulation in cardiac blood vessels. They further studied based on these findings and finally completed the present invention.

The present invention provides the following inventions.
[1] A prophylactic and/or therapeutic agent for a cardiovascular complication of diabetes, the agent comprising a compound for inhibiting neutral lipid accumulation in cardiovascular tissue or cells.
[2] The prophylactic and/or therapeutic agent according to [1], wherein the compound for inhibiting neutral lipid accumulation is a medium-chain fatty acid and/or a medium-chain triglyceride, the medium-chain fatty acid is a $C_{8-12}$ saturated fatty acid, and the medium-chain triglyceride is a simple or mixed acid triglyceride composed of a $C_{8-12}$ saturated fatty acid.
[3] The prophylactic and/or therapeutic agent according to [1] or [2], wherein the cardiovascular complication of diabetes is a disease with neutral lipid accumulation in a cardiac blood vessel.
[4] The prophylactic and/or therapeutic agent according to [3], wherein the cardiac blood vessel is stenosed or occluded by accumulated neutral lipid.
[5] The prophylactic and/or therapeutic agent according to any one of [1] to [3], wherein the cardiovascular complication of diabetes is a disease with a sign of myocardial hypertrophy or diffuse or concentric coronary artery stenosis.
[6] The prophylactic and/or therapeutic agent according to any one of [1] to [4], wherein the cardiovascular complication of diabetes is diabetic arteriosclerosis, a disease resulting from diabetic arteriosclerosis, diabetic nephropathy, diabetic retinopathy, or diabetic neuropathy.
[7] The prophylactic and/or therapeutic agent according to [6], wherein the diabetic arteriosclerosis is atherosclerosis.
[8] The prophylactic and/or therapeutic agent according to [6], wherein the disease resulting from diabetic arteriosclerosis is cerebrovascular disease, ischemic heart disease, or arteriosclerosis obliterans.
[9] The prophylactic and/or therapeutic agent according to [8], wherein the cerebrovascular disease is cerebral infarction or moyamoya disease.
[10] The prophylactic and/or therapeutic agent according to [8], wherein the ischemic heart disease is angina pectoris, myocardial infarction, arrhythmia, or heart failure.
[11] The prophylactic and/or therapeutic agent according to any one of [2] to [10], wherein the medium-chain fatty acid is one or more saturated fatty acids selected from a group consisting of caprylic acid, nonanoic acid, 8-methylnonanoic acid, and capric acid.
[12] The prophylactic and/or therapeutic agent according to any one of [2] to [11], wherein the medium-chain fatty acid is 8-methylnonanoic acid and/or capric acid.

[13] An agent for degrading neutral lipid for administration into a cardiac blood vessel of a diabetic patient or non-human mammal with a cardiovascular complication of diabetes, the agent comprising a compound for inhibiting neutral lipid accumulation in cardiovascular tissue or cells.
[14] The agent for degrading neutral lipid according to [13], wherein the compound for inhibiting neutral lipid accumulation is a medium-chain fatty acid and/or a medium-chain triglyceride, the medium-chain fatty acid is a $C_{8-12}$ saturated fatty acid, and the medium-chain triglyceride is a simple or mixed acid triglyceride composed of a $C_{8-12}$ saturated fatty acid.
[15] A method for preventing or treating a cardiovascular complication of diabetes, the method comprising a step of administering a compound for inhibiting neutral lipid accumulation in cardiovascular tissue or cells to a diabetic patient or non-human mammal with a cardiovascular complication of diabetes.
[16] The method according to [15], wherein the compound for inhibiting neutral lipid accumulation is a medium-chain fatty acid and/or a medium-chain triglyceride, the medium-chain fatty acid is a $C_{8-12}$ saturated fatty acid, and the medium-chain triglyceride is a simple or mixed acid triglyceride composed of a $C_{8-12}$ saturated fatty acid.
[17] The method according to [15] or [16], wherein the cardiovascular complication of diabetes is a disease with neutral lipid accumulation in a cardiac blood vessel.
[18] The method according to any one of [15] to [17], wherein the cardiovascular complication of diabetes is a disease with a sign of myocardial hypertrophy or diffuse or concentric coronary artery stenosis.
[19] Use of a compound for inhibiting neutral lipid accumulation in cardiovascular tissue or cells in production of a prophylactic or therapeutic drug for a cardiovascular complication of diabetes.
[20] The use according to [19], wherein the compound for inhibiting neutral lipid accumulation is a medium-chain fatty acid and/or a medium-chain triglyceride, the medium-chain fatty acid is a $C_{8-12}$ saturated fatty acid, and the medium-chain triglyceride is a simple or mixed acid triglyceride composed of a $C_{8-12}$ saturated fatty acid.
[21] The use according to [19] or [20], wherein the cardiovascular complication of diabetes is a disease with neutral lipid accumulation in a cardiac blood vessel.
[22] The use according to any one of [19] to [21], wherein the cardiovascular complication of diabetes is a disease with a sign of myocardial hypertrophy or diffuse or concentric coronary artery stenosis.
[23] A compound for inhibiting neutral lipid accumulation in cardiovascular tissue or cells for use to prevent or treat a cardiovascular complication of diabetes.
[24] The compound according to [23], wherein the compound for inhibiting neutral lipid accumulation is a medium-chain fatty acid and/or a medium-chain triglyceride, the medium-chain fatty acid is a $C_{8-12}$ saturated fatty acid, and the medium-chain triglyceride is a simple or mixed acid triglyceride composed of a $C_{8-12}$ saturated fatty acid.
[25] A compound for inhibiting neutral, lipid accumulation for use to improve the metabolism of neutral lipid in cardiovascular tissue or cells or improve a vascular function in a cardiovascular complication of diabetes.
[26] An agent for improving the metabolism of neutral lipid in cardiovascular tissue or cells in a cardiovascular complication of diabetes, the agent comprising (i) a $C_{8-12}$ medium-chain fatty acid and/or (ii) a medium-chain triglyceride that is a simple or mixed acid triglyceride composed of a $C_{8-12}$ medium-chain fatty acid.
[27] An agent for improving a vascular function in a cardiovascular complication of diabetes, the agent comprising (i) a $C_{8-12}$ medium-chain fatty acid and/or (ii) a medium-chain triglyceride that is a simple or mixed acid triglyceride composed of a $C_{8-12}$ medium-chain fatty acid.

Advantageous Effects of Invention

The prophylactic and/or therapeutic agent of the present invention has a most remarkable prophylactic or therapeutic effect at present on diabetic cardiovascular complications with neutral lipid accumulation in cardiac blood vessels in a diabetic patient. The prophylactic and/or therapeutic agent of the present invention may not necessarily contain an additional medicinal component (such as eicosapentaenoic acid, docosahexaenoic acid, and arachidonic acid) for treating diabetic cardiovascular complications because such a medicinal component is not an essential active component for obtaining a prophylactic or therapeutic effect. The present invention need not any additional medicinal component to be used in combination with the compound for inhibiting neutral, lipid accumulation and therefore has no risk of adverse effects caused by such a medicinal component. The prophylactic and/or therapeutic agent of the present invention also has a particularly remarkable alleviating (prophylactic or therapeutic) effect on diabetic cardiovascular complications with neutral lipid accumulation in cardiovascular tissue or cells. The agent for degrading neutral lipid for use in a cardiac blood vessel of the present invention can degrade neutral lipid accumulated in cardiovascular tissue or cells of a diabetic patient or non-human mammal with diabetes.

DESCRIPTION OF EMBODIMENTS

Figure 1:
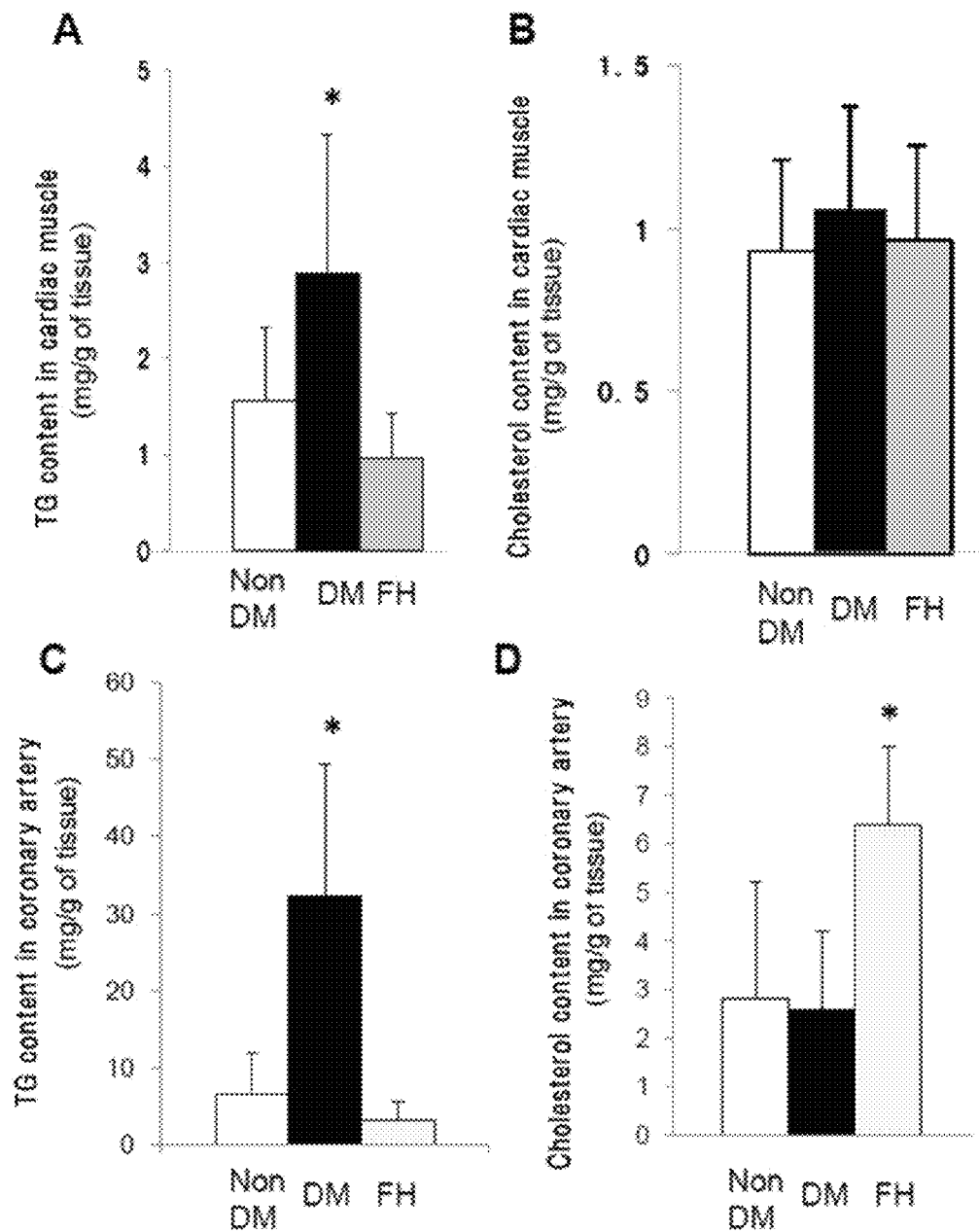
FIG. 1 is the results of the analysis of accumulation of neutral lipid and cholesterol in Experimental Example 2.

The prophylactic and/or therapeutic agent for diabetic cardiovascular complications of the present invention is characterized by containing, as an active ingredient, a compound for inhibiting neutral lipid accumulation in cardiovascular tissue or cells. In the present invention, the term "accumulation" of neutral lipid refers to an increase in the weight of neutral lipid or an increase in the size of neutral lipid mass. In the present invention, the term "degradation" of neutral lipid refers to a decrease in the weight of neutral lipid or a decrease in the size of neutral lipid mass. In the present invention, diabetes may be type 1 diabetes or type 2 diabetes. In the present invention, the term "cardiac blood vessel", or "cardiovascular", refers to cardiac muscle, coronary arteries, aortas, branched and peripheral arteries that branch from an aorta, and arterioles. In the present invention, the term "cardiovascular cell" refers to cardiomyocites and peripheral cells thereof, vascular smooth muscle cells, and vascular endothelial cells and peripheral cells thereof. In the present invention, the term "cardiovascular tissue" refers to an aggregation formed from these cells.

Diagnosis of diabetes is based on the Japanese criteria that follow. The criteria of The Japan Diabetes Society (JDA; 1999) define diabetes as a state that exhibits any of fasting plasma glucose (FPG) of 126 mg/dl or more, 2-hour plasma glucose (2hPG) after 75 g oral glucose tolerance test (OGTT) of 200 mg/dl or more, random plasma glucose of 200 mg/dl or more, and hemoglobin A1c (hereinafter, called HbA1c) of 6.5% (international standard value (=value according to NGSP: National Glycohemoglobin Standardization Program)) or more.

A state that belongs neither to the diabetic state as described above nor to "a state that exhibits fasting plasma glucose of less than 110 mg/dl or 2-hour plasma glucose after 75 g oral glucose tolerance test (75 g OGTT) of less than 140 mg/dl" (normal type) is called a "borderline type" (impaired glucose regulation: IGR). The diabetes in the present invention may include diabetes of the borderline type. The diabetes in the present invention may also include Impared Glucose Tolerance (IGT) and Impaired Fasting Glucose (IFG). Impared Glucose Tolerance is a state that exhibits fasting plasma glucose of less than 126 mg/dl and 2-hour plasma glucose after 75 g oral glucose tolerance test of 140 mg/dl or more and less than 200 mg/dl. Impaired Fasting Glucose is a state that exhibits fasting plasma glucose of 110 mg/dl or more and less than 126 mg/dl and 2-hour plasma glucose after 75 g oral glucose tolerance test of less than 140 mg/dl.

The cardiovascular complication of diabetes of the present invention is not particularly limited provided that it is a disease with neutral lipid accumulation in tissue or cells of cardiac muscle or blood vessels, and is preferably a disease with blood vessels stenosed or occluded by neutral lipid accumulated in blood vessels, a disease caused by the stenosis or occlusion, or a disease caused by neutral lipid accumulation in cardiac muscle. Preferable from a clinical standpoint are diabetic cardiovascular complications with a sign of myocardial hypertrophy and/or diffuse or concentric coronary artery stenosis because a remarkable prophylactic and/or therapeutic effect is exhibited on them. Specific examples of the cardiovascular complication of diabetes of the present invention include diabetic arteriosclerosis; diseases resulting from diabetic arteriosclerosis; and microangiopathy such as diabetic nephropathy, diabetic retinopathy, and diabetic neuropathy. The blood vessel affected in the cardiovascular complication of diabetes is not particularly limited, and examples thereof include cardiac, renal, and cerebral blood vessels and blood vessels in upper and lower limbs. The cardiac blood vessels are not particularly limited, and examples thereof include coronary arteries, which are preferable. The renal blood vessels are not particularly limited, and examples thereof include renal arteries. The cerebral blood vessels are not particularly limited, and examples thereof include cerebral arteries. Diabetes herein includes type 1 diabetes and type 2 diabetes, and type 2 diabetes is preferable.

Diabetic arteriosclerosis is not particularly limited provided that it has neutral lipid accumulation in blood vessels, and preferable examples thereof include atherosclerosis. In the present invention, in order that an excellent prophylactic or therapeutic effect may be exhibited, preferred as atherosclerosis is that in which an atheromatous lump (plaque) on a vascular wall is formed from neutral lipid accumulated in the blood vessels, and particularly preferable is that with a stenosed or occluded blood vessel. In order that a remarkable prophylactic and/or therapeutic effect may be exhibited, a case where symptoms are not alleviated by a cholesterol-lowering agent and/or surgical treatment (coronary angio- plasty) is preferable. The cholesterol-lowering agent is not particularly limited provided that it is a known cholesterol-lowering agent.

Examples of the diseases resulting from diabetic arteriosclerosis include cerebrovascular disease (CVD), ischemic heart disease (IHD), arteriosclerosis obliterans (ASO), vascular dysfunction, and endothelial dysfunction. It has become clear that these diseases when combined with diabetes are more serious than when occurring alone and difficult to treat, and the prophylactic and/or therapeutic agent of the present invention can exhibit a remarkable therapeutic effect on these conditions as well. Examples of cerebrovascular disease include cerebral infarction and moyamoya disease. Examples of cerebral infarction include a stroke, atherothrombotic cerebral infarction, and lacunar infarction. Ischemic heart disease is not particularly limited provided that it is a disease in which a blood flow to cardiac muscle is interrupted by the occlusion, stenosis, or the like of coronary arteries to cause heart disorder, and examples thereof include angina pectoris, myocardial infarction, arrhythmia, heart failure, and arteriosclerotic coronary artery disease. Examples of angina pectoris include angina of effort such as stable angina, unstable angina, and crescendo angina; and angina decubitus such as vasospastic angina. Examples of myocardial infarction include acute myocardial infarction (AMI), recent myocardial infarction, and old myocardial infarction. The present invention has an alleviating effect not only on a stenosed or occluded blood vessel but also on a smooth muscle cell, a cardiomyocite, or the like that does not contract or relax due to accumulated neutral lipid (in angina pectoris, for example), enabling its contraction and relaxation.

Examples of diabetic nephropathy include Kimmelstiel-Wilson syndrome. Examples of diabetic retinopathy include simple retinopathy, pre-proliferative retinopathy, and proliferative retinopathy. Examples of diabetic neuropathy include polyneuropathy; mononeuropathy multiplex such as amaurosis; dysautonomia such as gastrointestinal disorders (constipation and diarrhea), dyshidrosis, orthostatic hypotension, and impotence; and sensory neuropathy such as peripheral numbness and neuralgia.

The compound for inhibiting neutral lipid accumulation in cardiovascular tissue or cells of the present invention can degrade neutral lipid in cardiovascular tissue or cells or inhibit and prevent neutral lipid accumulation in cardiac blood vessels. The compound for inhibiting neutral lipid accumulation is not particularly limited provided that it is a compound capable of inhibiting neutral lipid accumulation in cardiovascular tissue or cells or degrading neutral lipid in cardiac blood vessels, and preferable examples thereof include a medium-chain fatty acid and/or a medium-chain triglyceride, which exerts a remarkable alleviating (prophylactic or therapeutic) effect. Medium-chain fatty acids (MC-FAs) and/or medium-chain triglycerides (MCTs) are generally classified into oil/fat, and therefore a preferable embodiment may be a pharmaceutical oil/fat composition. A medium-chain fatty acid as an active ingredient of the present invention is preferably a $C_{8-12}$ saturated fatty acid, and for greater activity to degrade neutral lipid to be obtained, a $C_{8-10}$ saturated fatty acid is more preferable and a $C_{9-10}$ saturated fatty acid is further preferable, because a fatty acid having 7 carbon atoms or less has no activity to degrade neutral lipid. Specifically, one or more kinds selected from the group consisting of caprylic acid, 8-methylnonanoic acid, nonanoic acid, and capric acid are more preferable, one or more kinds selected from the group consisting of nonanoic acid, 8-methylnonanoic acid, and capric acid are further preferable, and 8-methylnonanoic acid and/or capric acid is particularly preferable.

The medium-chain triglyceride used in the present invention is generally called MCT (Medium Chain Triglyceride), and may be a simple or mixed acid triglyceride. As the medium-chain triglyceride, for example, a simple or mixed acid triglyceride composed of $C_{8-12}$ medium-chain fatty acids such as coconut fatty acids can be used. A simple or mixed acid triglyceride composed of $C_{8-10}$ saturated fatty acids is preferable, and for greater activity to degrade neutral lipid, a simple acid triglyceride composed of a $C_{9-10}$ saturated fatty acid (100% capric acid, for example) is more preferable. In the cases where a mixed acid triglyceride is used, the ratio of the constituent medium-chain fatty acids of the mixed acid triglyceride may be determined as appropriate provided that the effects of the invention can be exhibited. Specifically, in the case of a mixed acid triglyceride composed of caprylic acid (C8)/capric acid (C10), the weight ratio that is caprylic acid:capric acid is usually within the range of 0:100 (except for the case where caprylic acid is exactly 0) to 90:10, preferably of 5:95 to 80:20, and more preferably of 5:95 to 75:25. The triglyceride can be produced by esterification of the medium-chain fatty acids and glycerol by a conventional procedure, but a commercial product thereof can be used for convenience.

The medium-chain triglyceride of the present invention can be a naturally-occurring one or one obtained by a synthetic method such as transesterification treatment using, as a raw material, an oil/fat composition containing a medium-chain triglyceride.

The esterification conditions are not particularly limited, and a non-catalytic, solventless reaction can be adopted, for example. Needless to say, a reaction using a catalyst and a solvent can also be adopted to obtain the medium-chain triglyceride of the present invention. While the reaction is allowed to proceed, water generated in the reaction is preferably removed. The method of removing water is preferably evaporation by heat, depressurization, or azeotropy using a water-insoluble solvent. The medium-chain triglyceride of the present invention can be obtained directly from oilseeds of a transgenic plant, and also can be produced by using, as a raw material, a medium-chain fatty acid derived from oilseeds of a transgenic plant. The medium-chain triglyceride can also be obtained by transesterification using, as a raw material, an oil/fat composition containing a medium-chain fatty acid or a triglyceride having a medium-chain fatty acid, through an enzymatic reaction with an alkaline catalyst or a lipolytic enzyme (lipase). The transesterification may be allowed to proceed using no solvent or using a water-insoluble solvent. Considering safety and oral application, the medium-chain triglyceride is preferably produced by transesterification using a lipolytic enzyme, but the production method is not limited thereto.

As the oil/fat composition containing a medium-chain triglyceride, an ordinary edible oil/fat containing a fatty acid constituted of $C_{6-12}$ fatty acids can be used. Specific examples thereof include soybean oil, rape oil, high-oleic rape oil, corn oil, sesame seed oil, sesame seed salad oil, Japanese basil oil, linseed oil, peanut oil, safflower oil, high-oleic safflower oil, sunflower oil, high-oleic sunflower oil, cottonseed oil, grape seed oil, macadamia oil, hazelnut oil, pumpkin seed oil, walnut oil, camellia oil, tea seed oil, perilla oil, borage oil, olive oil, rice bran oil, wheat germ oil, palm oil, palm kernel oil, coconut oil, cocoa butter, beef tallow, lard, chicken fat, milk fat, fish oil, seal oil, algae oil, these oils/fats the ratios of saturation of which are lowered for quality improvement, and hydrogenated oils/fats thereof and fractionated oils/fats thereof.

Examples of the lipolytic enzyme include lipases derived from the genus *Alcaligenes*, the genus *Candida*, the genus *Rhizopus*, the genus *Mucor*, and the genus *Pseudomonas*, and phospholipase A derived from liver, and particularly preferable are lipases derived from the genus *Candida* and the genus *Rhizopus*. The species of the enzyme can be selected as appropriate depending on conditions.

The method of transesterification using a lipolytic enzyme is not particularly limited, and a specific example thereof is shown below. The reaction temperature is adjusted to within the range of 40 to 100° C., at which the lipolytic enzyme adequately exhibits its activity, and the lipolytic enzyme is added to a raw material mixture at a proportion of 0.005 to 10% by mass, followed by transesterification for 2 to 48 hours. The reaction is allowed to proceed desirably at normal pressure under a nitrogen stream. The completion of the reaction is confirmed by gas chromatography analysis of the triglyceride composition of the reaction product. The reaction product is washed with water and is then dried, followed by decolorization and deodorization by conventional procedures. In the cases where a medium-chain fatty acid is used, after the termination of the reaction, free fatty acids are preferably removed with a thin film evaporator.

Specific examples of the method for producing the medium-chain triglyceride include a method in which glycerol is mixed with fatty acids that are caprylic acid and capric acid derived from palm kernel, oil or coconut oil, and the mixture is heated for dehydration condensation to bind caprylic acid or capric acid to glycerol, followed by distillation for purification. In this way, production of the medium-chain triglyceride can be carried out using no solvent nor catalyst.

When the compound for inhibiting neutral lipid accumulation is a medium-chain fatty acid and/or a medium-chain triglyceride, for example, the prophylactic and/or therapeutic agent of the present invention can be produced by blending the medium-chain fatty acid and/or the medium-chain triglyceride or by blending or mixing oils/fats and the like that contain the medium-chain fatty acid and/or the medium-chain triglyceride.

Containing the compound for inhibiting neutral lipid accumulation in cardiovascular tissue or cells, the prophylactic and/or therapeutic agent of the present invention can degrade neutral lipid accumulated in blood vessels, improve the metabolism of neutral lipid in cardiovascular tissue or cells in diabetic cardiovascular disease, and improve vascular functions, in a diabetic patient or a diabetic non-human mammal so as to prevent or treat diabetic cardiovascular complications.

In the prophylactic and/or therapeutic agent of the present invention, the compound (preferably the medium-chain fatty acid and/or the medium-chain triglyceride mentioned above) for inhibiting neutral lipid accumulation is an essential component, while a long-chain fatty acid or a glycerol fatty acid ester containing a long-chain fatty acid may not be necessarily contained.

The prophylactic and/or therapeutic agent for diabetic cardiovascular complications according to the present invention contains the medium-chain fatty acid and/or the medium-chain triglyceride specified above as an active ingredient, and is preferably combined, where appropriate, with any pharmacologically acceptable pharmaceutical carrier to produce a pharmaceutical formulation composition in a common form. The dosage form thereof is not particularly limited, and examples thereof include oral solid formulations such as tablets, capsules, troches, pills, powders, and granules; oral liquid formulations such as syrups, emulsions, and suspensions; and parenteral formulations such as external formulations, suppositories (rectal suppositories, urethral suppositories, vaginal suppositories, and the like), injectables (intravenous injectables, arterial injectables, intramuscular injectables, subcutaneous injectables, intradermal injectables, intraperitoneal injectables, intraspinal injectables, and epidural injectables), eye drops, pulmonary formulations, nasal formulations, and liposome formulations. A known coating method may be further adopted, where appropriate, to produce a sustained release formulation, a multilayered tablet, a sugar-coated tablet, a gelatin-coated tablet, and the like. The injectable may be mixed with a common replacement fluid containing, for example, dextrose and amino acids (including N-acylated derivatives of L-tyrosine, L-methionine, L-cystine, L-cysteine, and the like), or prepared as a dry product to be made into its liquid form on use. The pH of the prophylactic and/or therapeutic agent is not particularly limited. In the case of an injectable, the pH is 5.5 to 8.5, preferably 6.0 to 8.0, and further preferably 6.5 to 7.5.

Usually the solid formulations preferably contain a pharmaceutical carrier that is used as an excipient, a disintegrating agent, a binder, a lubricant, a fluidizing agent, a filler, or the like. For liquid preparations, a solvent, a dissolution promoter, a suspending agent, a tonicity-adjusting agent, a buffer, and an anesthetic are exemplified. Any known additives that are generally used in the field of formulation such as preserving agents, antioxidizing agents, colorants, sweeteners, absorption promoters, pH-adjusting agents, humectants, adsorbents, preservatives, stabilizers, and antioxidants can also be used where appropriate. These can be used alone or as a combination of two or more of these depending on the desired form of formulation. Specific examples of the pharmaceutical carrier are shown below, but the pharmaceutical carrier is not limited to these examples.

The excipient is not particularly limited, and examples thereof include lactose, caster sugar, granulated sugar, D-mannitol, D-sorbitol, corn starch, dextrin, cyclodextrin, microcrystalline cellulose, crystalline cellulose, carboxymethylcellulose (CMC), carboxymethylcellulose calcium, sodium carboxymethyl starch, low-substituted hydroxypropylcellulose, gum arabic, and light silicic anhydride.

The disintegrating agent is not particularly limited, and examples thereof include starch, agar-agar, gelatin powder, carboxymethylcellulose, calcium carboxymethylcellulose, sodium carboxymethylcellulose, sodium carboxymethyl starch, croscarmellose sodium, crospovidone, low-substituted hydroxypropylcellulose, hydroxypropyl methylcellulose (HPMC), methylcellulose, crystalline cellulose, calcium carbonate, sodium hydrogen carbonate, and sodium alginate.

The binder is not particularly limited, and examples thereof include hydroxypropylcellulose, hydroxypropyl methylcellulose, polyvinylpyrrolidone, crystalline cellulose, caster sugar, dextrin, starch, gelatin, carmellose sodium, gum arabic, and polyvinylpyrrolidone. The fluidizing agent is not particularly limited, and examples thereof include light silicic anhydride and magnesium stearate. The lubricant is not particularly limited, and examples thereof include magnesium stearate, calcium stearate, talc, and colloidal silica. The filler is not particularly limited, and examples thereof include cellulose, mannitol, and lactose.

The solvent is not particularly limited, and examples thereof include purified water, ethanol, propylene glycol, polyethylene glycol, macrogol, sesame seed oil, maize oil, and olive oil.

The dissolution promoter is not particularly limited, and examples thereof include propylene glycol, D-mannitol, benzyl benzoate, ethanol, triethanolamine, sodium carbonate, and sodium citrate.

The suspending agent is not particularly limited, and examples thereof include benzalkonium chloride, carmellose, hydroxypzopylcellulose, propylene glycol, polyvinylpyrrolidone, methylcellulose, glyceryl stearate, sodium lauryl sulfate, lecithin, and polyvinyl alcohol.

The tonicity-adjusting agent is not particularly limited, and examples thereof include dextrose, D-sorbitol, sodium chloride, D-mannitol, and glycerol. The buffer is not particularly limited, and examples thereof include phosphates (sodium hydrogen phosphate, for example), acetates (sodium acetate, for example), citrates (sodium carbonate), and citrates (sodium citrate, for example). The anesthetic is not particularly limited, and examples thereof include benzyl alcohol.

The preserving agent is not particularly limited, and examples thereof include ethyl p-hydroxybenzoate, chlorobutanol, benzyl alcohol, sodium dehydroacetate, and sorbic acid.

The antioxidizing agent is not particularly limited, and examples thereof include sodium sulfite and ascorbic acid. The colorant is not particularly limited, and examples thereof include food dyes (Food Red Nos. 2 and 3 and Food Yellow Nos. 4 and 5, for example) and β-carotene. The sweetener is not particularly limited, and examples thereof include sodium saccharin, dipotassium glycyrrhizate, and aspartame. The absorption promoter is not particularly limited, and examples thereof include quaternary ammonium bases and sodium lauryl sulfate. The pH-adjusting agent is not particularly limited, and examples thereof include citrates, phosphates, carbonates, tartrates, fumarates, acetates, and amino acid salts. The humectant is not particularly limited, and examples thereof include glycerol and starch. The adsorbent is not particularly limited, and examples thereof include starch, lactose, kaolin, bentonite, and colloidal silicic acid. The preservative is not particularly limited, and examples thereof include quaternary ammoniums such as benzalkonium chloride, benzethonium chloride, and cetylpyridinium chloride, p-hydroxybenzoic acid esters such as methyl p-hydroxybenzoate, ethyl p-hydroxybenzoate, propyl p-hydroxybenzoate, and butyl p-hydroxybenzoate, benzyl alcohol, phenylethyl alcohol, sorbic acid and salts thereof, thimerosal, chlorobutanol, and sodium dehydroacetate. The stabilizer is not particularly limited, and examples thereof include casein and sodium caseinate. Examples of the antioxidant include tert-butylhydroquinone, butylated hydroxyanisole, butylated hydroxytoluene, and α-tocopherol, and derivatives thereof.

The medium-chain fatty acid and/or the glycerol fatty acid ester containing a medium-chain fatty acid in the formulation of the present invention is an oily component, and therefore a nutritionally and physiologically functional component that is highly soluble therein such as vitamin A, vitamin D, vitamin E, ascorbyl fatty acid esters, lignan, coenzymes Q, phospholipids, triterpenes, orizanol, and choline bitartrate can be added thereto.

The route of administration may be either oral administration or parenteral administration by, for example, intravenous, subcutaneous, intramuscular, or intraperitoneal injection, and is preferably determined, as appropriate, depending on the age, disease state, and other conditions of the patient.

The prophylactic and/or therapeutic agent of the present invention can be administered to either a human or a non-human mammal via an oral route or a parenteral route (topically, intrarectally, or intravenously, for example). Examples of the non-human mammal include mice, rats, hamsters, guinea pigs, rabbits, cats, dogs, pigs, cows, horses, sheep, monkeys, and apes. The amount of the active ingredient in the prophylactic and/or therapeutic agent of the present invention is not particularly limited and is determined, as appropriate, depending on the disease state, the form of administration, and the like, usually being about 0.5 to 100% by mass, preferably about 1 to 100% by mass, further preferably about 5 to 100% by mass, and particularly preferably about 10 to 100% by mass in the whole pharmaceutical formulation. The dose or dosage/administration is not particularly limited and varies based on the age, sex, body weight, severity of disease, and the like of the patient. Generally, a daily dose to an adult is usually about 0.01 to 10000 mg and preferably about 10 to 6000 mg in terms of the total amount of active ingredients, and is preferably administered at once or divided into several doses (2 to 4 doses, for example).

The prophylactic and/or therapeutic agent of the present invention may further contain or be used concomitantly with a known cholesterol-lowering agent, thrombolytic, oral antihyperglycemic agent, or the like as an additional active ingredient provided that the effects of the invention are not impaired. The present invention also includes a kit for preventing and/or treating diabetic cardiovascular complications, the kit containing such a therapeutic drug in addition to the prophylactic and/or therapeutic agent for diabetic cardiovascular complications of the present invention. The kit may further contain written instructions.

The known cholesterol-lowering agent according to the present invention is not particularly limited, and examples thereof include HMG-CoA reductase inhibitors (statin drugs such as atorvastatin, pitavastatin, lovastatin, rosuvastatin, pravastatin, simvastatin, and fluvastain, for example) and fibrate drugs such as gemfibrozil, clofibrate, bezafibrate, fenofibrate, clinofibrate, and simfibrate. The known thrombolytic according to the present invention is not particularly limited, and examples thereof include tissue plasminogen activator (t-PA), urokinase, and streptokinase. The known oral antihyperglycemic agent according to the present invention is not particularly limited, and examples thereof include sulfonylurea (SU) drugs such as glibenclamide, gliclazide, and glimepiride; drugs for alleviating insulin resistance such as biguanide (BG) drugs (metformin hydrochloride and buformin hydrochloride, for example) and thiazolidine drugs (pioglitazone hydrochloride, for example); α-glucosidase inhibitors such as acarbose, voglibose, and miglitol; short-acting insulin secretagogues such as nateglinide, mitiglinide calcium hydrate, and repaglinide; and dipeptidyl peptidase (DPP) IV inhibitors such as sitagliptin, vildagliptin, and alogliptin.

The present invention also relates to an agent for degrading neutral lipid for administration into a cardiac blood vessel of a diabetic patient or non-human mammal with a cardiovascular complication of diabetes, the agent containing a compound for inhibiting neutral lipid accumulation in cardiovascular tissue or cells.

The compound for inhibiting neutral lipid accumulation in cardiovascular tissue or cells as an active ingredient of the agent for degrading neutral lipid for use in a cardiac blood vessel is the same as explained above. Containing the compound (preferably a medium-chain fatty acid and/or a medium-chain triglyceride) for inhibiting neutral lipid accumulation, the agent for degrading neutral lipid of the present invention can degrade neutral lipid accumulated in a blood vessel of a diabetic patient or non-human mammal with a cardiovascular complication of diabetes.

The agent for degrading neutral lipid for use in a cardiac blood vessel of the present invention, the agent containing the compound for inhibiting neutral lipid accumulation as an essential component may or may not contain, and is preferably devoid of, a long-chain fatty acid and a glycerol fatty acid ester containing a long-chain fatty acid.

The agent for degrading neutral lipid for use in a cardiac blood vessel according to the present invention contains, as an active ingredient, the compound (preferably the medium-chain fatty acid and/or the medium-chain triglyceride specified above) for inhibiting neutral lipid accumulation, and is preferably combined, where appropriate, with any pharmacologically acceptable pharmaceutical carrier to produce a pharmaceutical formulation composition in a common form in the same manner as for the prophylactic and/or therapeutic agent. The same dosage form, pharmaceutical carrier, route of administration, and subject of administration as for the prophylactic and/or therapeutic agent are adopted.

The amount of the active ingredient in the agent for degrading neutral lipid is not particularly limited and is determined, as appropriate, depending on the disease state, the form of administration, and the like as is for the prophylactic and/or therapeutic agent, usually being about 0.5 to 100% by weight and preferably about 1 to 100% by weight in the whole pharmaceutical formulation. The dose or dosage/administration is not particularly limited and varies based on the age, sex, body weight, severity of disease, and the like of the patient. Generally, a daily dose to an adult is usually about 0.01 to 10000 mg and preferably about 10 to 6000 mg in terms of the total amount of active ingredients, and is preferably administered at once or divided into several doses (2 to 4 doses, for example).

The present invention also relates to a method for preventing or treating cardiovascular complications of diabetes, the method comprising a step of administering a compound (preferably the medium-chain fatty acid and/or the medium-chain triglyceride specified above) for inhibiting neutral lipid accumulation in cardiovascular tissue or cells to a diabetic patient or non-human mammal, with a cardiovascular complication of diabetes. The same dosage form, pharmaceutical carrier, and route of administration as for the prophylactic and/or therapeutic agent are adopted for the compound for inhibiting neutral lipid accumulation to be administered in this method.

The dose or dosage/administration of the active ingredient in the method is not particularly limited provided that it is a medically effective amount, and varies based on the age, sex, body weight, severity of disease, and the like of the patient. Generally, a daily dose to an adult is usually about 0.01 to 10000 mg and preferably about 10 to 6000 mg in terms of the amount of the active ingredient, and is preferably administered at once or divided into several doses (2 to 4 doses, for example).

The method for preventing or treating cardiovascular complications of diabetes may also comprise, prior to the administration step, (1) a step of identifying a site where neutral lipid accumulates, and subsequent to step (1), may further comprise, where appropriate, (2) a step of separating a cell or organ where neutral lipid accumulates from a diabetic patient or non-human mammal with a cardiovascular complication of diabetes (hereinafter, may be simply called "subject").

In step (1) of identifying a site where neutral lipid accumulates, the method for identifying a site where neutral lipid accumulates is not particularly limited and can be a known method. Examples of the method include a CT scan and catheterization by which tissue is sampled to give a cell specimen that is then subjected to Oil Red O staining or microscopic observation.

In step (2) of separating a cell or organ where neutral lipid accumulates from a diabetic patient or a diabetic non-human mammal, the method for separating a cell or organ where neutral lipid accumulates from a subject is not particularly limited and can be a known method.

The present invention also relates to use of a compound (preferably the medium-chain fatty acid and/or the medium-chain triglyceride specified above) for inhibiting neutral lipid accumulation in cardiovascular tissue or cells in production of a prophylactic or therapeutic drug for diabetic cardiovascular complications. When the compound is used in combination with the various pharmaceutical carriers described above, a prophylactic or therapeutic drug for diabetic cardiovascular complications can be produced. In the production of a capsule formulation, for example, the compound for inhibiting neutral lipid accumulation is mixed with the various pharmaceutical carriers described above and the resultant mixture is encapsulated in a hard gelatin capsule or a soft capsule. In the production of an injectable formulation, the compound is mixed with the various pharmaceutical carriers described above, for example, a solvent or a tonicity-adjusting agent.

Another embodiment of the present invention may be a compound (preferably the medium-chain fatty acid and/or the medium-chain triglyceride specified above) for inhibiting neutral lipid accumulation in cardiovascular tissue or cells for use to prevent or treat diabetic cardiovascular complications. Use of the compound for inhibiting neutral lipid accumulation in cardiovascular tissue or cells can prevent or treat diabetic cardiovascular complications, as described above.

Another embodiment of the present invention may be a compound (preferably the medium-chain fatty acid and/or the medium-chain triglyceride specified above) for inhibiting neutral lipid accumulation for use to improve the metabolism of neutral lipid in cardiovascular tissue or cells or improve vascular functions, in diabetic cardiovascular complications. Use of the compound for inhibiting neutral lipid accumulation can improve neutral lipid metabolism in cardiovascular tissue or cells or improve vascular functions, in a patient or non-human mammal with a cardiovascular complication of diabetes, as described above.

Another embodiment of the present invention may be an agent for improving vascular functions in diabetic cardiovascular complications, the agent comprising the medium-chain fatty acid and/or the medium-chain triglyceride specified above. Use of the medium-chain fatty acid and/or the medium-chain triglyceride specified above can improve vascular functions in diabetic cardiovascular complications, as described above. When the medium-chain fatty acid and/or the medium-chain triglyceride is used in combination with the various pharmaceutical carriers described above, the agent for improving vascular functions can be produced.

The agent for improving vascular functions of the present invention, the agent containing the medium-chain fatty acid and/or the medium-chain triglyceride as an essential component may or may not contain, and is preferably devoid of, a long-chain fatty acid and a glycerol fatty acid ester containing a long-chain fatty acid.

Vascular functions can be evaluated by a known vascular endothelial reaction recorder such as a commercially available product named Endo-PAT (trade name: Endo-PAT 2000, CCI Corporation). On an Endo-PAT test, a value (RHI: Reactive Hyperemia Index) of 2.10 or more is normal, while a value of 1.67 or less is a criterion for determining vascular dysfunction. Use of the agent for improving vascular functions of the present invention can improve vascular functions (to 2.10 or more (RHI) on an Endo-PAT test, for example).

Another embodiment of the present invention may be an agent for improving the metabolism of neutral lipid in cardiovascular tissue or cells in diabetic cardiovascular complications, the agent containing the medium-chain fatty acid and/or the medium-chain triglyceride specified above. Use of the medium-chain fatty acid and/or the medium-chain triglyceride specified above can improve neutral lipid metabolism in diabetic cardiovascular complications, as described above. When the medium-chain fatty acid and/or the medium-chain triglyceride is used in combination with the various pharmaceutical carriers described above, the agent for improving neutral lipid metabolism can be produced.

The agent for improving neutral lipid metabolism in cardiovascular tissue or cells of the present invention, the agent containing the medium-chain fatty acid and/or the medium-chain triglyceride as an essential component may or may not contain, and is preferably devoid of, a long-chain fatty acid and a glycerol fatty acid ester containing a long-chain fatty acid.

Neutral lipid metabolism in cardiac blood vessels can be determined from the results of BMIPP (15(-p-iodophenyl)-3-(R,S)-methyl pentadecanoic acid) scintigram with use of a radioactive analog of a long-chain fatty acid. A low washout rate (%), determined from an early image and a delayed image, suggests slow degradation of long-chain fatty acids and a tendency of neutral lipid to accumulate or increase. The method and the device to obtain a BMIPP scintigram are not particularly limited, and can be a known method and a known device. A method using Cardiodine (registered trademark) injectable (trade name, $^{123}$I-BMIPP, Nihon Medi-Physics Co., Ltd.) can be used, for example. Use of the agent for improving neutral lipid metabolism in cardiovascular tissue or cells of the present invention can raise a washout rate, that is, improve neutral lipid metabolism (by reducing the tendency of neutral lipid to accumulate or decreasing neutral lipid mass, for example).

Another embodiment of the present invention may be a functional food for preventing, treating, or alleviating diabetic cardiovascular complications, the food containing a compound for inhibiting neutral lipid accumulation. The term "functional food" refers to a food that is produced or processed by using a raw material or a component having functionality useful for humans, where the term "functionality" refers to the quality of modifying a nutrient balance in terms of the organization and functions of a human body or the quality of providing useful health effects such as physiological actions. The functional food includes foods with health claims such as specified functional foods. The functional food can contain a pharmaceutical carrier that is used in production of the prophylactic and/or therapeutic agent provided that the effects of the invention are not impaired and safety as food is maintained, and can also contain a known food additive that is approved to be added to functional foods. The amount of the known pharmaceutical carrier or the known food additive is not particularly limited provided that the effects of the invention are not impaired and safety as food is maintained. The amount of an active ingredient in the functional food is not particularly limited, and is usually about 0.5 to 100% by weight and is preferably about 1 to 100% by weight relative to the total amount.

EXAMPLES

The present invention will be described more specifically by experimental examples and examples. These examples are, however, by no means limitative of the scope of the present invention, and various modifications can be made by a person with ordinary skill in the art without departing from the technical spirit of the present invention.

Experiments in Experimental Examples 1 to 3 used a diabetic patient group consisting of 10 diabetic patients (4 males, 6 females, average age±standard deviation (SD): 74.7±7.0) who had died of heart disease and a non-diabetic subject group with almost the same variation in age and sex as that of the diabetic patients, consisting of non-diabetic subjects (4 males, 6 females, average age±standard deviation (SD): 70.0±12.0) who had died of a disease except for heart disease.

Experimental Example 1

The hearts of the 10 diabetic patients who had died of heart disease while receiving adequate traditional therapies were dissected. Clinical pictures and pathological findings are as follows.

The average BMI of the patients was 21.3. The clinical diagnoses for them were myocardial infarction, angina pectoris, heart failure, and the like. The duration of diabetes was 15.3±9.7 years. The patients had been receiving therapy with insulin or an oral antihyperglycemic agent. Their dyslipidemia had been treated with a statin and/or a fibrate, and their serum LDL-cholesterol, which was 96.2±17 (standard value: 140 mg/dL or less), and serum TG, which was 126±41 (standard value: 150 mg/dL or less), had been adequately controlled. The hearts examined were heavy (534.5±87 g), with plaques formed in the three coronary arteries in each case indicating diffuse concentric stenosis. Fibrosis and/or infarct were observed in part of the cardiac muscle. The standard weight of heart is 272±1.5 g for male and 233±1.5 g for female (The Japanese Society of Pathology).

Each patient had been suffering from diabetes for a long time (4 years to 30 years) and also had myocardial infarction, angina pectoris, and/or heart failure. The results of dissection revealed that some cases had a stenosed or occluded coronary artery even though the LDL cholesterol level was lowered to the standard value or below by a cholesterol-lowering agent. In these cases, although the serum TG levels did not exceed the standard value, lesions of severe coronary arteriosclerosis were observed in multiple branches and cardiac muscle hypertrophied (heart weight increased). In more detail, coronary angiography on these patients showed diffuse stenosis in their left and right coronary arteries, and pathological observation by the naked eye confirmed diffuse concentric stenosis.

Experimental Example 2

In addition to the diabetic patient group and the non-diabetic subject group, 3 dissection specimens (n=3) derived from familial hypercholesterolemia (FH) as a typical example of cholesterol-induced arteriosclerosis were analyzed for accumulation of neutral lipid and cholesterol. The results are shown in FIG. 1. In the figure, A shows the amount (mg/g of tissue) of neutral lipid in cardiac muscle, B shows the amount (mg/g of tissue) of cholesterol in cardiac muscle, C shows the amount (mg/g of tissue) of neutral lipid in coronary arteries, and D shows the amount (mg/g of tissue) of cholesterol in coronary arteries. Non DM indicates non-diabetic subjects, DM indicates diabetic patients, and FH indicates patients with familial hypercholesterolemia. In the figure, * indicates statistical significance (p<0.001, Dunnett's test) realtive to the other two data.

The results in FIG. 1 revealed significant accumulation of neutral lipid (TG) in cardiac muscle and coronary arteries of the diabetic patients (see FIGS. 1A and C).

Experimental Example 3

Figure 2:
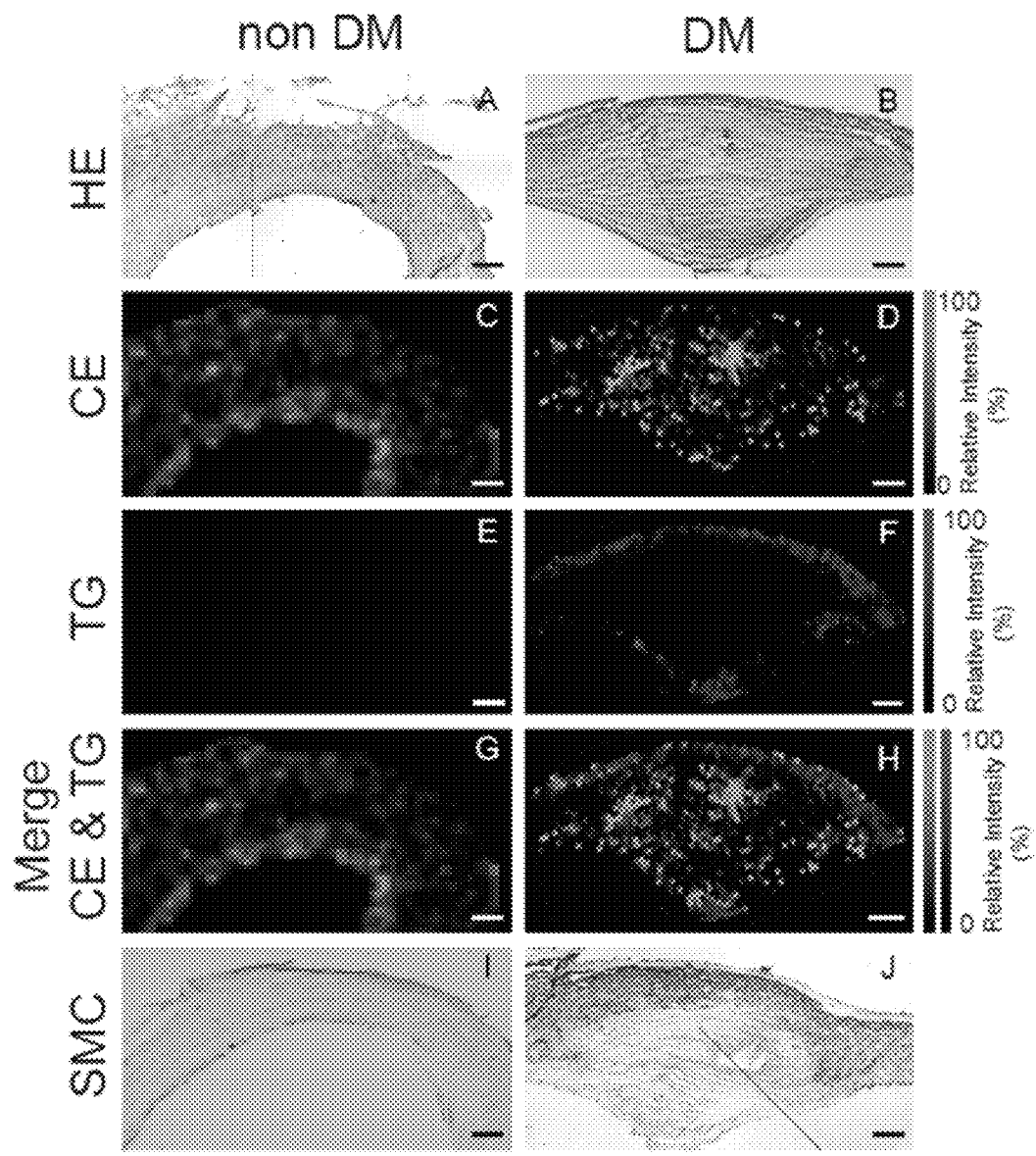
FIG. 2 is the results of the analysis of the pattern of lipid distribution in coronary arteries in a diabetic patient and a non-diabetic subject in Experimental Example 3.

The specimens derived from the diabetic patient group and the non-diabetic subject group were subjected to HE staining and immunostaining to analyze the pattern of lipid distribution in the coronary arteries. FIG. 2 (C to H) shows the results of observation by an imaging mass spectrometer (vacuum type, trade name: Ultraflex II TOF/TOF, manufactured by Bruker Daltonics Inc.). HE staining and immunostaining were performed by conventional procedures. A and B are the results of HE staining, C to H are the results of observation by the imaging mass spectrometer, and I and J are the results of immunostaining. C and D are the results of observation of cholesterol esters, E and F are the results of observation of neutral lipid, and G and H are a synthetograph generated from C and E and a synthetograph generated from D and F, respectively. Contrast in C to H reflects detection intensity. Non DM indicates non-diabetic subjects, while DM indicates diabetic patients.

In the non-diabetic subject group, while diffuse of the cholesterol ester (CE) signals to coronary arterial walls was confirmed (FIG. 2C), little neutral lipid (TG) was observed (FIG. 2E). Surprisingly, in the diabetic patient group, the neutral lipid signals were distinctly differentiated from the cholesterol ester signals. The signals of CE were localized at the center of the lesion, while ones of TG were localized at the intimal, medial, and adventitial regions near the center of arteriosclerosis nidus (FIGS. 2D, F). Most of the TG signals overlapped smooth muscle cells (SMC) (FIGS. 2F and J). These findings confirmed that neutral lipid accumulation in smooth muscle cells occurred in arteriosclerotic coronary artery disease in diabetic patients.

Example 1

A male patient in his 60s who had had type 2 diabetes for 10 years, had experienced cerebral infarction, had been suffering from angina symptoms for 5 years, had received a statin and traditional therapy for diabetes with no alleviation of symptoms, and had been evaluated as in no need of coronary artery intervention showed diffuse stenosis in a cardiac CT, an abnormal BMIPP scintigram, and vascular endothelial dysfunction, and thereby was determined to have neutral lipid accumulation in cardiac blood vessels or neutral lipid metabolism disorder. The vascular endothelial functions were examined using a vascular endothelial reaction recorder (brand name: Endo-PAT 2000, CCI Corporation). The patient received dietetic treatment with 3 g of a medium-chain triglyceride (trade name: O.D.O, composition: medium-chain triglyceride (caprylic acid:capric acid=75:25 (by weight)) composed of caprylic acid and capric acid alone, manufactured by Nisshin OilliO Group, Ltd.) 3 times a day, at each meal, for 30 days. The number (time) of doses of NTG sublingual tablet in 1 month, fasting plasma glucose (mg/dL), HbA1c (%), vascular functions (Endo-PAT) (Index), BMIPP scintigrams (an early image and a delayed image), and washout rate (%) were recorded. The BMIPP scintigrams were obtained using Cardiodine (registered trademark) Injectable (trade name, $^{123}$I-BMIPP, Nihon Medi-Physics Co., Ltd.) by a known method. The washout rate was calculated by the following formula.

Washout rate=(Counts in early image−Counts in delayed image)/(Counts in early image)×100

The results are shown in Table 1. The BMIPP scintigrams showed non-uniform distribution before MCT intake, and an increase in the washout rate was observed after 30 days of MCT intake. The cholesterol level of the male patient did not exceed the standard value in Table 1.

TABLE 1

| Evaluation items | Before MCT intake | After 30 days of MCT intake | Standard value |
|---|---|---|---|
| Number of doses of NTG sublingual tablet in 1 month (times) | 6 | 0 | — |
| Fasting plasma glucose (mg/dL) | 155 | 105 | 70-110 |
| HbA1c(%) | 7.2 | 6.5 | 4.6-6.2 |
| Vascular function (Endo-PAT) (Index) | 1.62 | 2.82 | 2.10 or more |
| BMIPP scintigram (early image) | Non-uniform distribution | Non-uniformity alleviated | — |
| Washout rate (%) | 32 | 42 | — |

(In the table, NTG denote nitroglycerin and the Endo-PAT value means RHI (Reactive Hyperemia Index).)

As shown in Table 1, the Endo-PAT value completely returned to normal from 1.62 to 2.82, indicating recovery of vascular functions. Angina symptoms were also alleviated. As is evident from FIG. 4, reduction in non-uniformity, an increase in washout rate, and improvement in the metabolism of neutral lipid in cardiac blood vessels were observed.

These results confirmed that the present invention had a remarkable therapeutic effect on diabetic cardiovascular complications that had become serious due to the presence of diabetes and were difficult to effectively treat with conventional drugs. It was also revealed that when a patient with a cardiovascular complication had neutral lipid accumulation, the present invention had an excellent prophylactic and/or therapeutic effect on the patient regardless of which of type 1 diabetes or type 2 diabetes the patient had. The present invention also has a remarkable therapeutic effect on a patient with diabetes and cardiovascular complications who suffers from anginal pain and/or heart failure symptoms even though no abnormality is observed in an electrocardiogram or coronary angiography and a patient with diabetes and cardiovascular complications who suffers from angina symptoms and/or heart failure symptoms but has no focal lesion in coronary arteries to which coronary artery intervention should be applied.

Example 2

Figure 3:
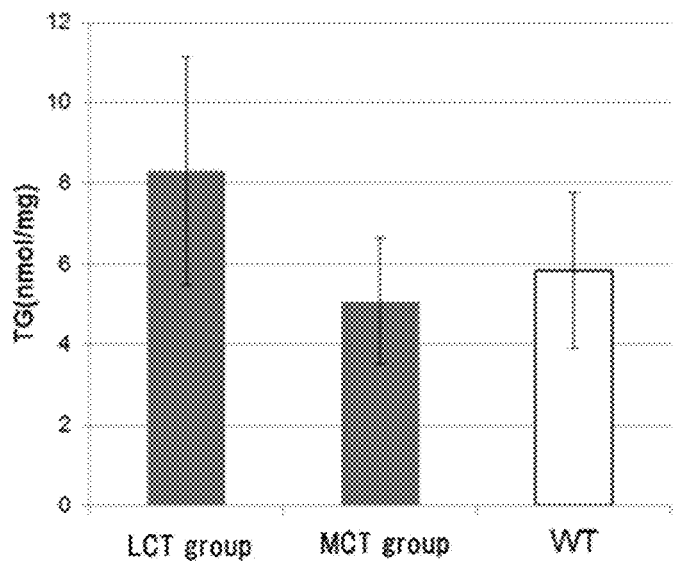
FIG. 3 is the results of the measurement (n=3) of neutral lipid contents in aortas in Example 2.

Diabetic model, mice (db/db mouse) purchased from Charles River Laboratories Japan, Inc. were fed with, as a prophylactic and/or therapeutic agent, a food composition containing the components shown in Table 2, and the amount of neutral lipid in the aorta was measured. Specifically, the mice had free access to the food composition containing the components shown in Table 2 used as a prophylactic and/or therapeutic agent for 4 weeks starting when turned 8 weeks old, and after sacrifice, lipid was extracted from the aorta to be subjected to an enzyme assay (n=3) for neutral lipid (TG) quantification. The enzyme assay was performed using a triglyceride quantification kit (manufacturer: BioVision, Inc., product code: K622-100). Diabetic model mice (db/db mouse) (LCT-administered group) (n=3) of the same kind to which the composition shown in Table 3 was administered were used as a control. The results are shown in FIG. 3. In FIG. 3, the MCT-administered group refers to the mice to which the composition containing the components shown in Table 2 was administered, the LCT-administered group refers to the mice to which the composition containing the components shown in Table 3 was administered, and WT denotes wild-type mice (n=3).

TABLE 2

| Components | Content (g) |
|---|---|
| Corn starch (manufactured by Nippon Starch Chemical) | 397.086 |
| Casein (manufactured by Wako Pure Chemical Industries) | 200 |
| α-Corn starch (manufactured by Nippon Starch Chemical) | 132 |
| Granulated sugar | 100 |
| Corn oil (main components: linoleic acid 56.1%, oleic acid 29.5%, linolenic acid 1.2%, saturated fatty acid 12.5%, manufactured by Nacalai Tesque) | 20 |
| O.D.O. (trade name, composition: medium-chain triglyceride (caprylic acid:capric acid = 75:25 (by weight)) composed of caprylic acid and capric acid alone, manufactured by Nisshin OilliO Group) | 50 |
| Cellulose (manufactured by Oriental Yeast) | 50 |
| Mineral mix (trade name: AIN-93G-MX, manufactured by CLEA Japan) | 35 |
| Vitamin mix (trade name: AIN-93VX, manufactured by CLEA Japan) | 10 |
| L-Cystine (product code: 2706, manufactured by Peptide Institute) | 3 |
| Choline bitartrate (manufactured by Tokyo Chemical Industry) | 2.5 |
| TBHQ (tert-butylhydroquinone) (manufactured by Wako Pure Chemical Industries) | 0.014 |
| Total | 1000 |

TABLE 3

| Components | Content (g) |
|---|---|
| Corn starch (manufactured by Nippon Starch Chemical) | 397.086 |
| Casein (manufactured by Wako Pure Chemical Industries) | 200 |
| α-Corn starch (manufactured by Nippon Starch Chemical) | 132 |
| Granulated sugar | 100 |
| Corn oil (main component: linoleic acid 56.1%, oleic acid 29.5%, linolenic acid 1.2%, saturated fatty acid 12.5%, manufactured by Nacalai Tesque) | 70 |
| Cellulose (manufactured by Oriental Yeast) | 50 |
| Mineral mix (trade name: AIN-93G-MX, manufactured by CLEA Japan) | 35 |
| Vitamin mix (trade name: AIN-93VX, manufactured by CLEA Japan) | 10 |
| L-Cystine (product code: 2706, manufactured by Peptide Institute) | 3 |
| Choline bitartrate (manufactured by Tokyo Chemical Industry) | 2.5 |
| TBHQ (tert-butylhydroquinone) (manufactured by Wako Pure Chemical Industries) | 0.014 |
| Total | 1000 |

As is evident from the results in FIG. 3, the present invention successfully reduced neutral lipid in aortas.

Example 3

A diabetic patient (male in his 40s) who was to have heart transplantation due to severe heart failure received dietetic treatment with a medium-chain triglyceride (trade name: O.D.O, composition: medium-chain triglyceride (caprylic acid:capric acid=75:25 (by weight)) composed of caprylic acid and capric acid alone, manufactured by Nisshin OilliO Group, Ltd.) for 50 days immediately before the heart transplantation, which was conducted 3 years after implantation of a left ventricular assist system (LVAS). The amount of neutral lipid (TG) accumulated in the apical cardiac muscle was examined. Another diabetic patient (male in his 40s), who served as a control, received no dietetic treatment with a medium-chain triglyceride in 3 years from LVAS implantation to heart transplantation.

The hearts removed at the time of heart transplantation were examined for the amount of neutral lipid accumulated in the coronary arteries. The patient who received the dietetic treatment was subjected to indirect calorimetry with an indirect calorimeter (manufactured by Yamato Scientific Co., Ltd.), and a respiratory quotient and a fat-burning rate before and a week after the initiation of the dietetic treatment were determined. In the dietetic treatment, lipid intake per day was 40 g, 10 g of which was from naturally-occurring food (in other words, 100% long-chain fatty acid) and the other 30 g was from a diet containing the medium-chain triglyceride as its only source of lipid. Both of the patients had been receiving a β-blocker, an ACE inhibitor (angiotensin-converting enzyme inhibitor), and an anticoagulant as a therapeutic agent for heart failure for 3 years. The patient who received the diet containing a medium-chain triglyceride did not take any other food because he developed cerebral embolism before the initiation of the dietetic treatment.

The TG content in cardiac muscle decreased in the patient who received the diet containing a medium-chain triglyceride from 42±8 (mg/g tissue) at the time of LVAS implantation to 28±4 (mg/g tissue) at the time of heart transplantation, while that in the patient without the dietetic treatment increased from 30±2 (mg/g tissue) at the time of LVAS implantation to 35±8 (mg/g tissue) at the time of heart transplantation.

The amount of TG accumulated in coronary arteries measured at the time of heart transplantation was 2.5±2 (mg/g tissue) for the former patient and 18±5 (mg/g tissue) for the latter patient, indicating that the amount of TG accumulated in cardiac muscle and coronary arteries in the patient who received the diet containing a medium-chain triglyceride was lower than that in the patient without the dietetic treatment.

The respiratory quotient of the patient who received the dietet containing a medium-chain triglyceride decreased from 0.95±0.02 (value before the dietetic treatment) to 0.82±0.03.

The fat-burning rate increased from 8±2 (g/day) to 53±10 (g/day), confirming that lipid degraded in the body.

These revealed that diet containing a medium-chain triglyceride was able to decrease the amount of neutral lipid accumulated in cardiac muscle and coronary arteries of a diabetic patient.

Example 4

Figure 4:
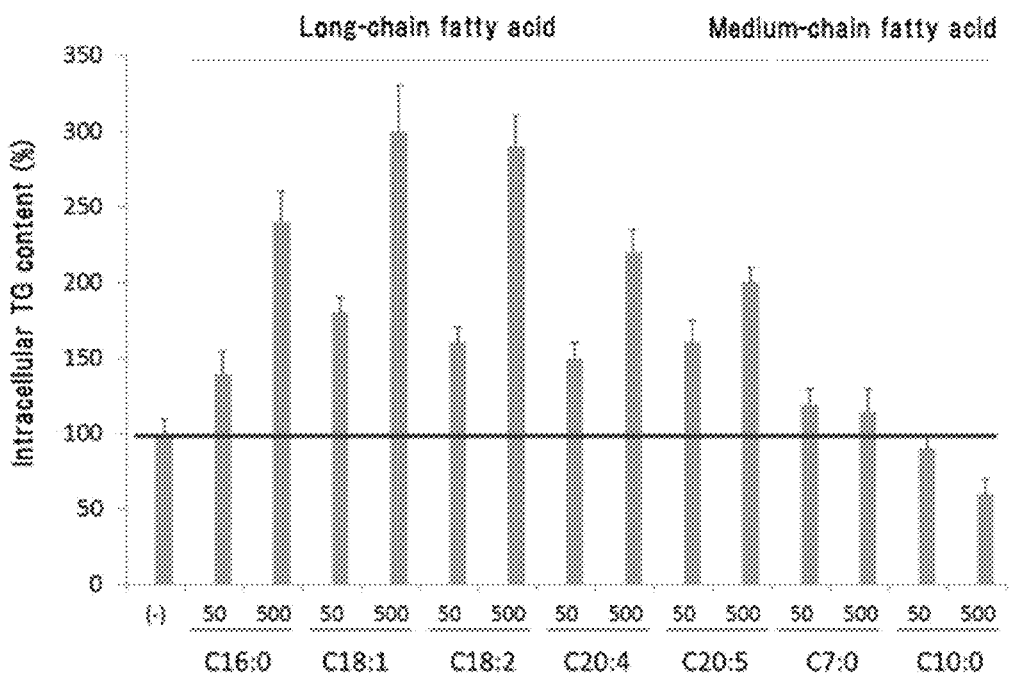
FIG. 4 is the results of the measurement of the influences of various fatty acids on neutral lipid contents in Example 4.
Figure 5:
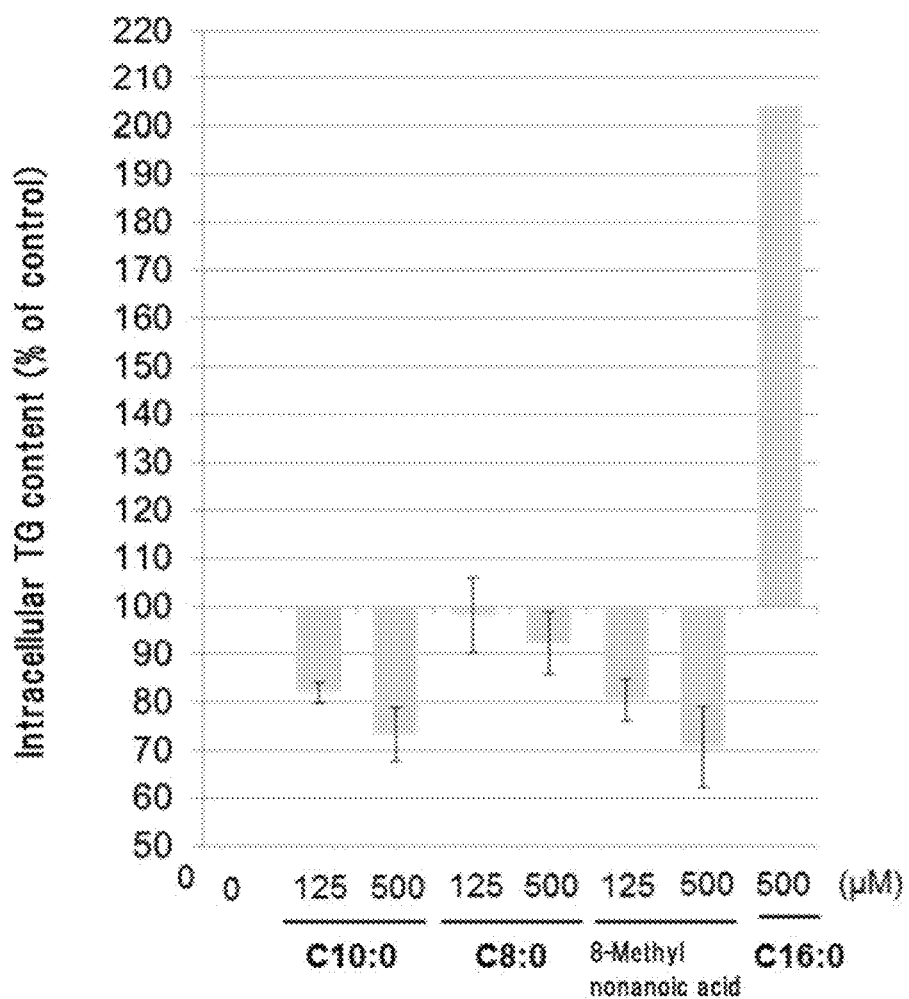
FIG. 5 is the results of the measurement of the influences of various fatty acids on neutral lipid contents in Example 4.

With the consent of the diabetic patient in Example 3, part of dermal tissue was harvested and was then subjected to primary culture (culture medium: DMEM/10% FBS) by Explant method, followed by repeated subculture to give a cell line. The resulting dermal fibroblast was examined for the influence of various fatty acids on an intracellular neutral lipid content. Specifically, the dermal specimen harvested from the patient was subjected to an in vitro enzyme assay using various fatty acids to measure an intracellular neutral lipid content. The enzyme assay was performed using a triglyceride quantification kit (manufacturer: BioVision, Inc., product code: K622-100). First, it was confirmed that cells derived from the patient had an accumulated intracelluar neutral lipid content of 0.35±0.03 (g of cell protein), which was about 5 times higher than that of dermal fibroblasts obtained from healthy non-diabetic subjects (0.07±0.03 (g of cell protein) in cells derived from 3 healthy subjects). To the patient's cells, the various fatty acids were added, and 2 days later, the cells were collected. The results are shown in FIG. 4 and FIG. 5. In the figures, (-) is a specimen to which no fatty acid was added (cultured as a control in DMEM/10% FBS alone). C16:0 is palmitic acid, C18:1 is oleic acid, C18:2 is linoleic acid, C20:4 is arachidonic acid, C20:5 is eicosapentaenoic acid (EPA), C7:0 is heptanoic acid, C8:0 is caprylic acid, and C10:0 is capric acid. Each of these was added to the cells so as to achieve 50 and 500 μM as shown in the figures.

As shown in FIG. 4, all of the long-chain fatty acids tested resulted in increased intracellular TG contents, while capric acid as a medium-chain fatty acid decreased intracellular TG. FIG. 5 shows a more detailed comparison of the activity of capric acid to decrease intracellular TG with the same activity of other medium-chain fatty acids. FIG. 5 revealed that capric acid and 8-methylnonanoic acid had great activity to decrease TG. Based on part of the results in FIG. 4 and FIG. 5, the influences of fatty acids on physiological activity are shown in Table 4.

TABLE 4

| Fatty acids | Intracellular TG-decreasing activity | Alternative energy activity |
|---|---|---|
| Heptanoic acid 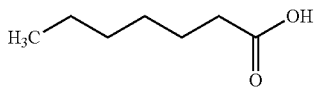 | 0 | 70 |
| Octanoic acid (caprylic acid) 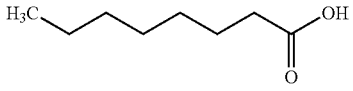 | 5 | 80 |
| Decanoic acid (capric acid) 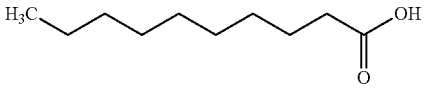 | 100 | 100 |

TABLE 4-continued

| Fatty acids | Intracellular TG-decreasing activity | Alternative energy activity |
|---|---|---|
| 8-Methylnonanoic acid | 100 | 100 |

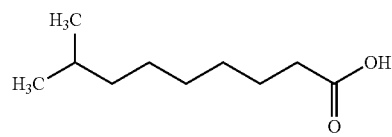

(The number of ATP to be generated is proportional to the carbon number, and therefore the alternative energy activity in the table is an estimated proportion calculated from the carbon number.)

FIG. 4 revealed that EPA, which is conventionally considered to be effective in treating diabetes, increased intracellular neutral lipid. Among the medium-chain fatty acids, heptanoic acid increased intracellular neutral lipid, while capric acid decreased intracellular neutral lipid. FIG. 5 indicates that use of the medium-chain fatty acid of the present invention successfully decreased intracellular neutral lipid.

Formulation Example 1

To distilled water for injection, 305.7 g of a medium-chain triglyceride (trade name: O.D.O, composition: medium-chain triglyceride (caprylic acid:capric acid=75:25 (by weight)) composed of caprylic acid and capric acid alone, manufactured by Nisshin OilliO Group, Ltd.) was added, and the resultant mixture was homogenized with a homomixer to give a coarse emulsion. To this, distilled water for injection was added to give a coarse emulsion in an amount of 1000 ml. The resulting coarse emulsion was emulsified with a Manton-Gaulin homogenizer (manufactured by Gaulin, 15M-8TA) to give an emulsion. To 403.8 ml of the resulting emulsion, 8 ml of a 2% aqueous L-histidine solution and distilled water for injection were added to achieve a total volume of 1600 ml. Citric acid was further added thereto to adjust the pH to 7.0. The resulting solution was dispensed in plastic bags, each of which was then hermetically sealed and subjected to steam sterilization (autoclave sterilization) under high pressure at 110° C. for 30 minutes to give an injectable. This solution can be administered to a patient after diluted with an appropriate amount of physiological saline.

INDUSTRIAL APPLICABILITY

The prophylactic and/or therapeutic agent for diabetic cardiovascular complications of the present invention is useful for preventing or treating diabetic cardiovascular complications in a diabetic patient, and is particularly useful for preventing or treating diabetic cardiovascular complications with neutral lipid accumulation in tissue or cells of cardiac muscle or blood vessels.

The invention claimed is:

1. A method for treating a cardiovascular complication of diabetes, the method comprising a step of administering a compound for inhibiting neutral lipid accumulation in cardiovascular tissue or cells to a diabetic patient or a diabetic non-human mammal with a cardiovascular complication of diabetes, the compound being a medium-chain triglyceride, the medium-chain triglyceride being a simple or mixed acid triglyceride composed of a saturated fatty acid, the saturated fatty acid being capric acid alone or caprylic acid and capric acid,
wherein the method excludes administering fish oil.

2. The method according to claim 1, wherein the cardiovascular complication of diabetes is a case where improvement is not achieved by a cholesterol-lowering agent and/or surgical treatment.

3. The method according to claim 1, wherein the cardiovascular complication of diabetes is a disease with neutral lipid accumulation in a cardiac blood vessel.

4. The method according to claim 3, wherein the cardiac blood vessel is narrowed or blocked by accumulated neutral lipid and is one or more selected from the group consisting of coronary arteries, aortas, branched and peripheral arteries that branch from an aorta, and arterioles.

5. The method according to claim 1, wherein the cardiovascular complication of diabetes is a disease with a sign of myocardial hypertrophy or diffuse or concentric coronary artery stenosis.

6. The method according to claim 1, wherein the cardiovascular complication of diabetes is diabetic arteriosclerosis, a disease resulting from diabetic arteriosclerosis, diabetic nephropathy, diabetic retinopathy, or diabetic neuropathy.

7. The method according to claim 6, wherein the diabetic arteriosclerosis is atherosclerosis.

8. The method according to claim 6, wherein the disease resulting from diabetic arteriosclerosis is cerebrovascular disease, ischemic heart disease, or arteriosclerosis obliterans.

9. The method according to claim 8, wherein the cerebrovascular disease is cerebral infarction or moyamoya disease.

10. The method according to claim 8, wherein the ischemic heart disease is angina pectoris, myocardial infarction, arrhythmia, or heart failure.

11. The method according to claim 1, wherein the compound is administered into a cardiac blood vessel.

* * * * *